(12) United States Patent
Yokomizo et al.

(10) Patent No.: US 8,857,627 B2
(45) Date of Patent: Oct. 14, 2014

(54) BLOOD PROCESSING FILTER

(75) Inventors: Tomohisa Yokomizo, Tokyo (JP); Morikazu Miura, Tokyo (JP)

(73) Assignee: Asahi Kasei Medical Co., Ltd., Tokyo (JP)

(*) Notice: Subject to any disclaimer, the term of this patent is extended or adjusted under 35 U.S.C. 154(b) by 173 days.

(21) Appl. No.: 13/334,226

(22) Filed: Dec. 22, 2011

(65) Prior Publication Data

US 2012/0160763 A1 Jun. 28, 2012

Related U.S. Application Data

(60) Provisional application No. 61/427,313, filed on Dec. 27, 2010.

(51) Int. Cl.
*A61M 1/34* (2006.01)
*B01D 35/28* (2006.01)
*B01D 35/30* (2006.01)
*A61M 1/02* (2006.01)
*A61M 1/36* (2006.01)

(52) U.S. Cl.
CPC ............... *A61M 1/02* (2013.01); *A61M 1/3636* (2014.02)
USPC ........... 210/435; 210/443; 210/450; 210/451; 210/445; 210/454; 210/455

(58) Field of Classification Search
None
See application file for complete search history.

(56) References Cited

U.S. PATENT DOCUMENTS

| 4,066,556 | A | 1/1978 | Vaillancourt |
| 5,792,133 | A * | 8/1998 | Rochat ........................... 604/406 |
| 2006/0049097 | A1 * | 3/2006 | Cavallini et al. .............. 210/435 |

FOREIGN PATENT DOCUMENTS

| EP | 0 526 678 | 12/1991 |
| JP | 53-54178 | 5/1978 |
| JP | 1-320064 | 12/1989 |
| JP | 7-267871 | 10/1995 |
| JP | 2006-507881 | 3/2006 |
| JP | 2006-246963 | 9/2006 |
| JP | 2008-289904 | 12/2008 |
| JP | 4435693 | 1/2010 |
| JP | 4411019 | 2/2010 |
| WO | 90/15660 | 12/1990 |
| WO | 92/20428 | 11/1992 |
| WO | 95/17236 | 6/1995 |

OTHER PUBLICATIONS

U.S. Appl. No. 13/252,288 to Tomohisa Yokomizo et al., filed Oct. 4, 2011.
International Preliminary Report on Patentability for PCT/JP2011/079705, mailed Jul. 11, 2013.
Japan Office action, mail date is May 20, 2014.

* cited by examiner

*Primary Examiner* — Benjamin Kurtz
(74) *Attorney, Agent, or Firm* — Greenblum & Bernstein, P.L.C.

(57) ABSTRACT

A blood processing filter including a flexible container (having an inlet and an outlet and a sheet-like filter member that is assembled in the flexible container) has a seal part that seals the flexible container and the filter member to form an effective filtration portion of the filter member and a partition part that seals the flexible container and the filter member to partition the effective filtration portion into a plurality of areas. The seal part and the partition part cooperate with the filter member to divide inside of the flexible container into three or more internal spaces including an inlet space that communicates with the inlet, and an outlet space that communicates with the outlet, and also form, as a blood channel, a channel that passes through each of three or more of the internal spaces and also passes multiple times through the filter member.

9 Claims, 9 Drawing Sheets

BLOOD PROCESSING FILTER

BACKGROUND OF THE INVENTION

Field of the Invention

The present invention relates to a blood processing filter for removing undesirable components such as aggregates and leukocytes from blood. In particular, the present invention relates to a precise and disposable blood processing filter for removing microaggregates and leukocytes which may cause side effects from whole blood preparations, erythrocyte preparations, thrombocyte preparations, blood plasma preparations and the like for blood transfusion.

It is becoming common for whole blood collected from a donor to be separated into blood component preparations such as an erythrocyte preparation, a thrombocyte preparation, and a blood plasma preparation and stored for later transfusion. Since microaggregates and leukocytes included in these blood preparations cause various side effects during blood transfusion, the number of occasions for removing these undesirable components before blood transfusion is increasing. The need for leukocyte removal in particular has been widely recognized in recent years. Legislation regarding removal of leukocytes from all kinds of blood preparations for blood transfusion before being used for transfusion has been introduced in an increasing number of countries.

The most common method of removing leukocytes from blood preparations is by processing blood preparations using a leukocyte removal filter. Conventionally, in many cases blood preparations have been processed using a leukocyte removal filter at the bedside when blood transfusion is performed. In recent years, however, to improve quality control of leukocyte-free preparations and efficiency of leukocyte removal operations, it is more common, particularly in developed countries, to process the blood preparations in blood centers before storing the blood preparations. Hereunder, leukocyte removal that is performed before storage is referred to as "pre-storage leukocyte removal".

A blood collection-separation set, typically consisting of two to four flexible bags, a tube connecting these bags, an anticoagulant, an erythrocyte preservation solution, a blood collection needle and the like has been used for collecting blood from a donor, separating the blood into several blood components, and storing the blood components. A system in which a leukocyte removal filter is incorporated into the aforementioned blood collection-separation set has been widely used as an optimum system for "pre-storage leukocyte removal". Such a system is called a "closed system" or an "integrated system" or the like. Such systems are disclosed in Japanese Patent Laid-Open No. 1-320064, International Publication No. WO 92/020428 and the like.

Conventionally, a filter element made from nonwoven fabric or a porous body packed in a hard container of polycarbonate or the like has been widely used as a leukocyte removal filter. However, because, in case of the hard container, the container has a low level of air permeability, there is the problem that it is difficult to apply steam sterilization, which is widely used as a sterilization process in blood collection-separation sets. In one type of closed system, leukocytes are first removed from the whole blood preparation after collecting the blood. Subsequently, after the leukocyte removal filter is separated, the leukocyte-free blood is centrifuged for separation into various components. In another type of closed system, the whole blood is first centrifuged to be divided into various blood components, and then the leukocytes are removed. In the latter case, the leukocyte removal filter is also centrifuged together with the blood collection-separation set. At such time, a hard container may damage bags and tubes, or the hard container itself may not withstand the stress and may break during centrifugation.

To solve these problems, flexible leukocyte removal filters have been developed in which the container is made of a material having excellent flexibility and steam permeability that is the same as or similar to the material used for the bags of the blood collection-separation set, and in fact blood processing filters in which a flexible container is directly welded to a filter member and the like are known (see Japanese Patent Laid-Open No. 7-267871 and International Publication No. WO 95/017236). According to this kind of leukocyte removal filter, for example, a flexible container is formed using a sheet-like material having flexibility, and an internal space of the flexible container is divided into one side and other side by a filter member. Ports that serve as an inlet and an outlet for blood are respectively provided on the one side and the other side into which the flexible container is divided by the filter member. Blood that flows from the inlet is discharged from the outlet after passing through the filter member one time.

According to the above described leukocyte removal filter, it can be expected that, as long as the raw material used to make filter members is the same, the capacity of a filter member that is thick and small to remove leukocytes and the like will be enhanced compared to a filter member that is thin and large. On the other hand, from the perspective of ease in assembling and, particularly, sealing the filter member, thinner filter members enable easier assembly and sealing of filter members therein. Further, a thin, large filter member is better for enabling the easy flow of blood. That is, according to the aforementioned leukocyte removal filter, respectively conflicting problems and advantages exist with respect to a case in which a filter member is thin and a case in which a filter member is thick, and it has been difficult to obtain a leukocyte removal filter that can provide the advantages of both kinds of filter members.

SUMMARY OF THE INVENTION

According to the present invention, there is provided a blood processing filter that easily obtains a desired filtration performance while providing the advantages of a thin filter member.

That is, one aspect of the present invention relates to a blood processing filter comprising a flexible container having an inlet and an outlet for blood, a sheet-like filter member that is assembled in the flexible container, a seal part that seals the flexible container and the filter member to form an effective filtration portion of the filter member, a partition part that seals the flexible container and the filter member to partition the effective filtration portion into a plurality of areas; wherein the seal part and the partition part cooperate with the filter member to divide inside of the flexible container into three or more internal spaces including an inlet space that communicates with the inlet, and an outlet space that communicates with the outlet, and also form, as a blood channel, a channel that passes through each of three or more of the internal spaces and also passes multiple times through the filter member. Note that, according to the present invention, the term "blood" includes blood preparations such as whole blood preparations, erythrocyte preparations, thrombocyte preparations and blood plasma preparations for blood transfusion and the like.

According to the above described blood processing filter, as a blood channel from the inlet to the outlet, a channel is formed that while passing through a plurality of internal spaces, also passes multiple times through the filter member. According to this blood processing filter, even when the filter member is thin, since blood passes through the filter member multiple times, a capacity to remove leukocytes and the like that is equal to a case in which the filter member is thick can be expected. Accordingly, advantages obtained in a case in which a filter member is thick can be enjoyed while maintaining advantages in terms of manufacture and filtration rate that are obtained when the filter member is thin.

According to the present invention, a form can also be adopted in which, in the above described blood processing filter, the flexible container includes a first container forming part, and a second container forming part that overlaps with the first container forming part in a manner that sandwiches the filter member therebetween and that is sealed to the first container forming part; wherein the seal part and the partition part form a plurality of the internal spaces on one side of the filter member and form one or a plurality of the internal spaces on other side of the filter member and, as the blood channel, form a channel that passes through the internal spaces formed on the one side of the filter member and through the internal space formed on the other side of the filter member in an alternating manner and also passes multiple times through the filter member.

In addition, according to the present invention, a form can be adopted in which, in the above described blood processing filter, the seal part and the partition part form a plurality of the internal spaces including the inlet space and the outlet space on the one side of the filter member and, on the other side of the filter member, form the internal spaces in a number that is one less than a number of the internal spaces on the one side of the filter member.

Further, according to the present invention, a form can be adopted in which, in the above described blood processing filter, the seal part and the partition part form a plurality of the internal spaces including the inlet space on the one side of the filter member and, on the other side of the filter member, form the internal spaces in a number that is identical to a number of the internal spaces on the one side of the filter member that include the outlet space.

Furthermore, according to the present invention, a form can be adopted in which, in the above described blood processing filter, the seal part and the partition part form the inlet space and the outlet space on the one side of the filter member and, on the other side of the filter member, form an intermediate space that can communicate with both of the inlet space and the outlet space through the filter member, and also form, as the blood channel, a channel that passes through the inlet space, the intermediate space, and the outlet space and also passes multiple times through the filter member.

Further, according to the present invention, a form can be adopted in which, in the above described blood processing filter, a surface area of the filter member that is exposed in the inlet space is greater than a surface area of a region that communicates with the outlet space within a surface area of the filter member that is exposed inside the intermediate space.

DESCRIPTION OF THE PREFERRED EMBODIMENTS

Embodiments of the present invention are described hereunder with reference to the drawings. Note that the term "blood" that is described in each of the following embodiments includes blood preparations such as whole blood preparations, erythrocyte preparations, thrombocyte preparations and blood plasma preparations for blood transfusion. Further, although various forms can be adopted for the external shape of the blood processing filter, such as a rectangular shape, a disc shape, an oval disc shape, and an elliptical shape, a rectangular shape is preferable for decreasing loss of materials when manufacturing the filters. Accordingly, in the following embodiments, an example in which the blood processing filter has a rectangular shape is described.

Figure 1:
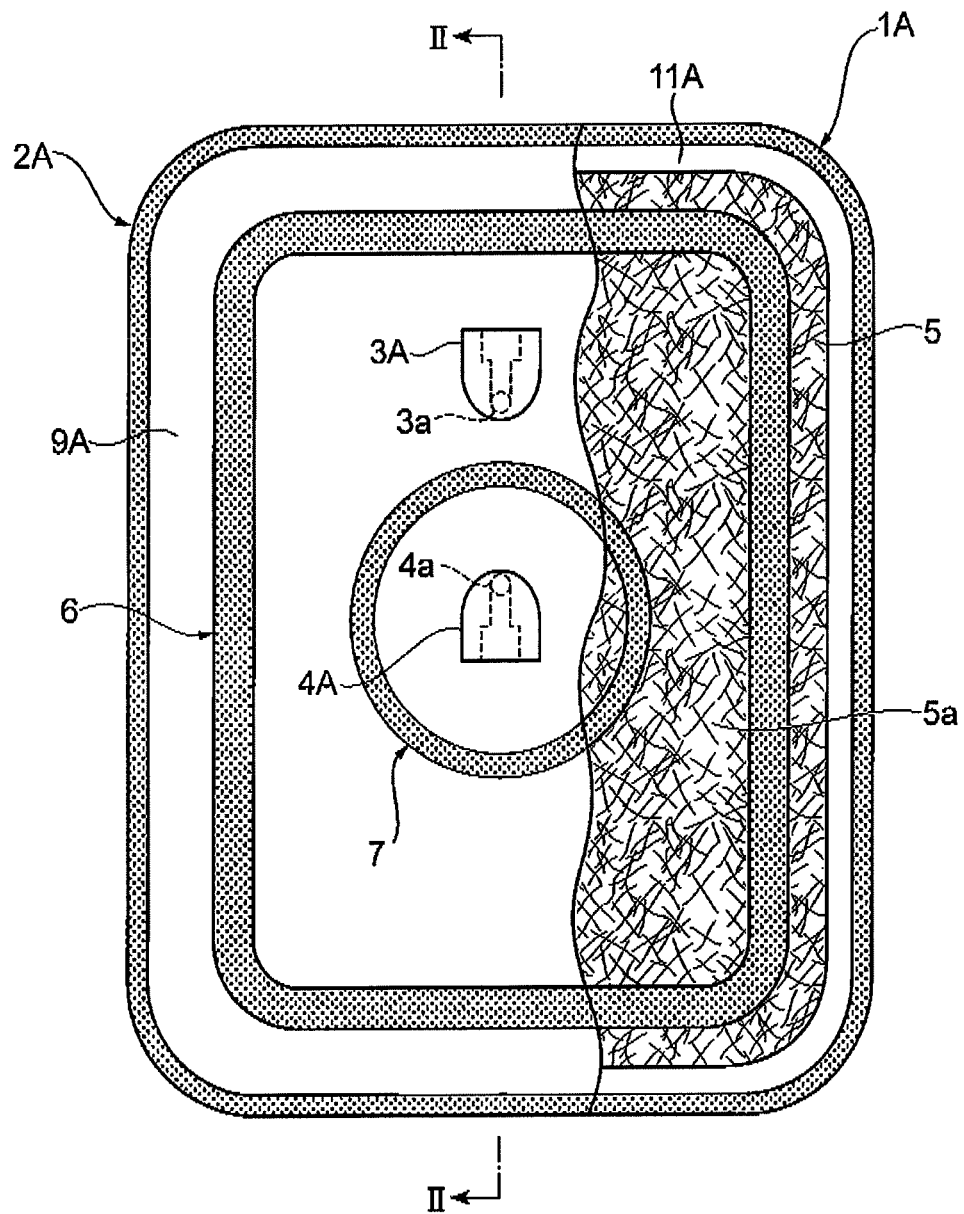
FIG. 1 is a plan view that illustrates one portion of a blood processing filter according to a first embodiment of the present invention, that is shown in a cut-away manner.
Figure 2:
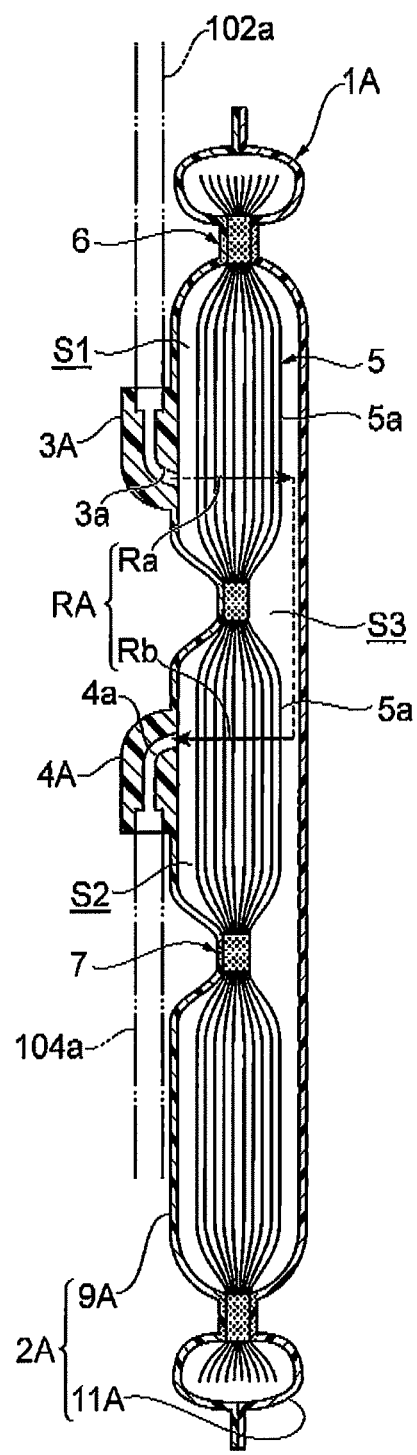
FIG. 2 is a cross-sectional view taken along a line II-II in FIG. 1.

First, a blood processing filter 1A relating to a first embodiment of the present invention is described referring to FIG. 1 and FIG. 2. The blood processing filter 1A includes a flexible container 2A having an inlet port 3A and an outlet port 4A for blood, and a sheet-like filter member 5 that is assembled in the flexible container 2A.

The flexible container 2A has a rectangular, flat shape. Here, the term "flat shape" means a shape having a thin thickness and a wide surface. The flexible container 2A includes a first container forming part 9A that has a rectangular sheet shape, and a second container forming part 11A that has a rectangular sheet shape. The first container forming part 9A and the second container forming part 11A overlap in a manner that sandwiches the rectangular-shaped filter member 5 therebetween, and the peripheries of the first container forming part 9A and the second container forming part 11A closely contact each other and are sealed in a band shape. In this connection, as used herein, the term "seal (to seal)" refers to fixing by bonding (including welding) to a degree that can prevent leakage of a liquid.

The inlet port 3A and the outlet port 4A are sealed in the first container forming part 9A. An inlet flow channel 3a that serves as an inlet that communicates with inside of the flexible container 2A is formed in the inlet port 3A. An outlet flow channel 4a that serves as an outlet that communicates with inside of the flexible container 2A is formed in the outlet port 4A.

The blood processing filter 1A also includes a seal part 6 that seals the flexible container 2A and the filter member 5 to form an effective filtration portion 5a of the filter member 5, and a partition part 7 that seals the flexible container 2A and the filter member 5 to partition the effective filtration portion 5a into a plurality of areas.

The seal part 6 and the partition part 7 cooperate with each area of the effective filtration portion 5a of the filter member 5 to divide the inside of the flexible container 2A into a plurality of internal spaces S1, S2, and S3 that include an inlet space S1 and an outlet space S2. The inlet space S1 is an internal space that communicates with the inlet flow channel 3a of the inlet port 3A. The outlet space S2 is an internal space that communicates with the outlet flow channel 4a of the outlet port 4A. The inlet space S1 and the outlet space S2 are formed on a side (one side) that faces the first container forming part 9A of the filter member 5. An intermediate space S3 that is a third internal space is formed on a side (other side) that faces the second container forming part 11A of the filter member 5.

The first container forming part 9A and the second container forming part 11A are sealed in a band shape along the periphery of the filter member 5 in a state in which the filter member 5 is clamped therebetween. A bonded area that is sealed in a rectangular ring shape along the periphery of the filter member 5 is the seal part 6.

The first container forming part 9A and the filter member 5 are sealed in a circular ring shape and in a band shape on an inner side that is surrounded by the seal part 6. A bonded area that is sealed in a ring shape on the inner side of the seal part 6 is the partition part 7.

The seal part 6 and the partition part 7 according to the present embodiment cooperate with each area of the effective filtration portion 5a of the filter member 5 to form the two internal spaces S1 and S2 on one side of the filter member 5, and to form the internal space S3 on the other side of the filter member 5 so that the number of internal spaces on the other side is one less than the number of internal spaces on the one side. Specifically, the inlet space S1 and the outlet space S2 are formed between the filter member 5 and the first container forming part 9A, and the intermediate space S3 is formed between the filter member 5 and the second container forming part 11A. The intermediate space S3 is not partitioned by the partition part 7, and is provided so as to be capable of communicating with both the inlet space 81 and the outlet space S2 through the filter member 5.

The surface area of the filter member 5 that is exposed inside the inlet space S1 is greater than the surface area of a region that communicates with the outlet space S2 within the surface area of the filter member 5 that is exposed inside the intermediate space S3.

The seal part 6 and the partition part 7 form, as a blood channel RA, a channel that passes through each of the internal spaces S1, S2, and S3, and also passes multiple times through the filter member 5. For example, in the case of the present embodiment, as the blood channel RA, the seal part 6 and the partition part 7 form an outward channel Ra that passes through the filter member 5 from the inlet space S1 towards the intermediate space S3, and a return channel Rb that passes through the filter member 5 from the intermediate space S3 towards the outlet space S2. As a result, the blood channel RA passes through the internal spaces S1 and S2 formed on one side of the filter member 5 and through the internal space S3 formed on the other side of the filter member 5 in an alternating manner.

Next, the material and shape and the like of each element constituting the blood processing filter 1A are described. As described in the foregoing, the flexible container 2A is formed by the first container forming part 9A and the second container forming part 11A. Any material that is commercially available as a sheet or a film can be used as a flexible resin that is used for the flexible container 2A. Examples of favorable materials include soft polyvinyl chloride; polyurethane; ethylene-vinyl acetate copolymer; polyolefin such as polyethylene and polypropylene; hydrogenated styrene-butadiene-styrene copolymer; a thermoplastic elastomer such as styrene-isoprene-styrene copolymer or the hydrogenated product thereof; and mixtures of the thermoplastic elastomer and a softening agent such as polyolefin or ethylene-ethyl acrylate. Since it can be considered that the material will contact with blood, preferable materials are soft polyvinyl chloride, polyurethane, and polyolefin that are used as the material of medical products such as blood bags, as well as thermoplastic elastomers containing these materials as major components, and more preferably the material is soft polyvinyl chloride.

Further, for example, a container described in Japanese Patent Laid-Open No. 7-267871 or a container described in International Publication No. WO 95/017236 can also be used as the flexible container 2A.

The filter member 5 is manufactured using a filter material constituted by a fibrous integrated body such as nonwoven fabric or woven fabric or by a porous body such as sponge. The filter member 5 according to the present embodiment may be coated with a hydrophilic polymer to make it easier for blood to wet the filter material. Further, to facilitate attachment of leukocytes to the filter member 5 when using the blood processing filter 1A to remove leukocytes from blood, a filter material that is coated with a polymer may be used.

Next, a method for manufacturing the blood processing filter 1A according to the present embodiment is described. According to this manufacturing method, for example, an installing step is performed in which the first container forming part 9A in which the inlet port 3A and the outlet port 4A have been sealed at predetermined positions and the filter member 5 are prepared, and the first container forming part 9A and the filter member 5 are arranged at predetermined positions.

After the installing step, a first sealing step is performed in which the partition part 7 is formed by sealing the first container forming part 9A and the filter member 5 in a band shape so as to surround the area in which the outlet port 4A is formed.

After the first sealing step, the second container forming part 11A is arranged at a predetermined position so as to sandwich the filter member 5 between the first container forming part 9A and the second container forming part 11A. Next, a second sealing step is performed in which the rectangular ring-shaped seal part 6 is formed by sealing the first container forming part 9A, the filter member 5, and the second container forming part 11A so as to surround the partition part 7 along the periphery of the filter member 5.

Although formation of the partition part 7 in the first sealing step, more specifically, sealing of the first container forming part 9A and the filter member 5 can be performed utilizing high frequency welding, the present invention is not limited thereto, and various kinds of bonding techniques, such as ultrasonic welding or thermal welding, can be used. Likewise, although sealing to form the seal part 6 in the second sealing step can be performed utilizing high frequency welding, the present invention is not limited thereto, and various kinds of bonding techniques, such as ultrasonic welding or thermal welding, can be used.

After the first sealing step and the second sealing step, a third sealing step is performed in which the first container forming part 9A and the second container forming part 11A are superimposed on each other so as to sandwich the filter member 5, and the peripheries of the first container forming part 9A and the second container forming part 11A are brought into close contact with each other and sealed in a band shape. Although sealing of the first container forming part 9A and the second container forming part 11A can be performed utilizing high frequency welding, the present invention is not limited thereto, and various kinds of bonding techniques, such as ultrasonic welding or thermal welding, can be used. Note that the third sealing step can also be performed at the same time as the second sealing step, or prior to the second sealing step.

According to the above described manufacturing method, a form is described in which the inlet port 3A and the outlet port 4A are previously sealed to the flexible container 2A. However, sealing may be performed after forming the partition part 7 and the seal part 6, or may be performed during the process of forming the partition part 7 and the seal part 6. Further, a method of sealing the inlet port 3A and the outlet port 4A to the flexible container 2A is not limited to high frequency welding, and any kind of bonding technique, such as thermal welding, can be used. Similarly to the flexible container 2A, various known materials can be used as the material of the inlet port 3A and the outlet port 4A.

Figure 3:
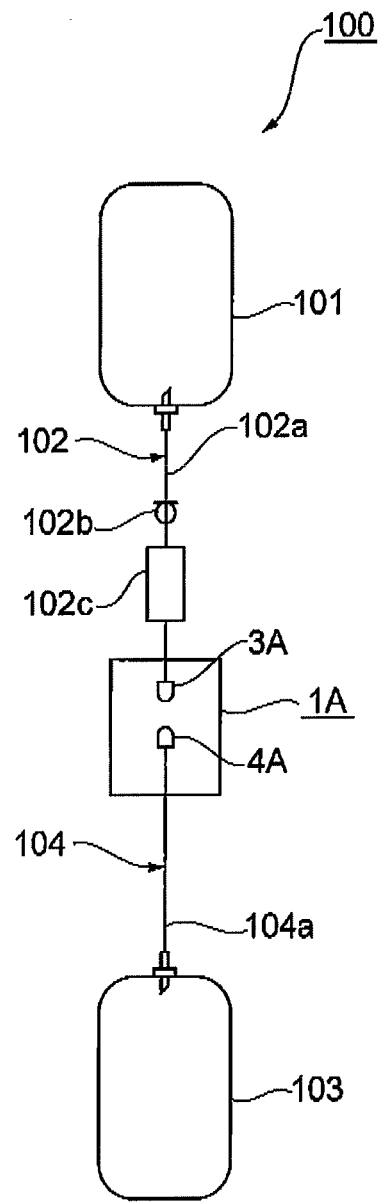
FIG. 3 is a front view that shows an outline of a blood processing system that includes the blood processing filter according to the first embodiment.

Next, a blood processing system 100 that includes the blood processing filter 1A according to the first embodiment is described (see FIG. 3).

The blood processing filter 1A can be used for filtering using gravitational force. For example, the blood processing system 100 to which the blood processing filter 1A is applied includes a reservoir bag 101 into which blood is filled after collection, the blood processing filter 1A, and a recovery bag 103 for accumulating blood after filtering. The reservoir bag 101 and the inlet port 3A of the blood processing filter 1A are connected to each other by a capillary tube 102a such as a blood tube. The recovery bag 103 and the outlet port 4A of the blood processing filter 1A are connected to each other by a capillary tube 104a such as a blood tube. Further, opening/closing means 102b such as a roller clamp that opens and closes a flow channel and a chamber 102c and the like are mounted in the capillary tube 102a on the upstream side. An inlet-side circuit 102 is formed by the capillary tube 102a, the opening/closing means 102b, and the chamber 102c and the like. An outlet-side circuit 104 is formed by the capillary tube 104a and the like on the downstream side.

The reservoir bag 101 into which blood is filled after collection is arranged at a position that is approximately 50 cm higher than the blood processing filter 1A. The recovery bag 103 in which blood is accumulated after filtering is arranged at a position that is approximately 100 cm lower than the blood processing filter 1A. A blood filtering process is performed by opening the flow channel of the blood processing system 100.

Next, the actions and effects of the blood processing filter 1A according to the present embodiment are described with reference to FIG. 1 to FIG. 3. In the blood processing filter 1A, as the blood channel RA from the inlet flow channel 3a to the outlet flow channel 4a, a channel is formed that, while passing through the plurality of internal spaces S1, S2, and S3, also passes multiple times through the filter member 5. According to the blood processing filter 1A, even though the filter member 5 is thin, since blood passes through the filter member 5 multiple times, it can be expected that the capacity to remove leukocytes and the like will be equal to a case in which the filter member 5 is thick. That is, an effect that is equal to a case in which a thick filter member is used can be obtained by dividing the effective filtration portion 5a of the filter member 5 by means of the partition part 7, and this effect is advantageous in reducing the material required as the filter member 5. Furthermore, the capacity to remove leukocytes and the like can be maintained even though less material is used.

Further, from the viewpoint of assembling the blood processing filter 1A, regardless of the fact that the thin filter member 5 is used, an effect is obtained that is equal to an effect obtained when adopting a form in which a small, thick filter member is used that is difficult to assemble. Accordingly, a welding workload when sealing the filter member 5 also decreases, and thus the blood processing filter 1A according to the present embodiment is also advantageous from the viewpoint of the assembly workload. Hence, advantages can be obtained in terms of ease of assembly and ease of sealing.

Further, according to the blood processing filter 1A, a first filtration (primary filtration) is performed when blood passes through the filter member 5 in the outward channel Ra of the blood channel RA, and a second filtration (secondary filtration) is performed when blood passes through the filter member 5 in the return channel Rb of the blood channel RA. During the primary filtration, removal of aggregates and the like is principally performed, and during the secondary filtration only blood from which aggregates and the like have been removed is filtered. In this case, in the primary filtration a certain area is necessary because there is a loss due to entry of aggregates and the like. On the other hand, in the secondary filtration, since the blood that is filtered has undergone filtration once and contains no aggregates and has a reduced amount of leukocytes, a filtration area that is smaller than the filtration area on the primary filtration side is sufficient for the secondary filtration side. Furthermore, in the blood processing filter 1A, since an area ratio between the filtration area on the primary filtration side and the filtration area on the secondary filtration side can be made an arbitrary area ratio, the area ratio can be optimized with ease. That is, according to the blood processing filter 1A, not only can the number of sheets of nonwoven fabric and the like constituting the filter member 5 as well as the overall area thereof be optimized in accordance with the blood to be filtered, the usage conditions, and required performance, but it is also possible to arbitrarily optimize the area ratio between the filtration area on the primary filtration side and the filtration area on the secondary filtration side.

In addition, according to the blood processing filter 1A, the surface area of the filter member 5 that is exposed in the inlet space S1 is greater than the surface area of a region that communicates with the outlet space S2 within the surface area of the filter member 5 that is exposed in the intermediate space S3. Hence, it is possible to enhance the primary filtration function, and efficiently perform the secondary filtration.

Further, in the blood processing filter 1A, since the intermediate space S3 exists between the outlet space S2 and the inlet space S1, when performing a filtration process, a negative pressure that arises in the outlet space S2 can be alleviated and uniform filtration can be performed.

In this connection, although according to the present embodiment a member is not adhered or the like on the one side or the other side of the filter member 5 in correspondence with the seal part 6 or the partition part 7, a configuration may also be adopted in which, for example, a frame sheet or the like for maintaining the strength of the partition part 7 is sealingly integrated with the filter member 5.

Figure 4:
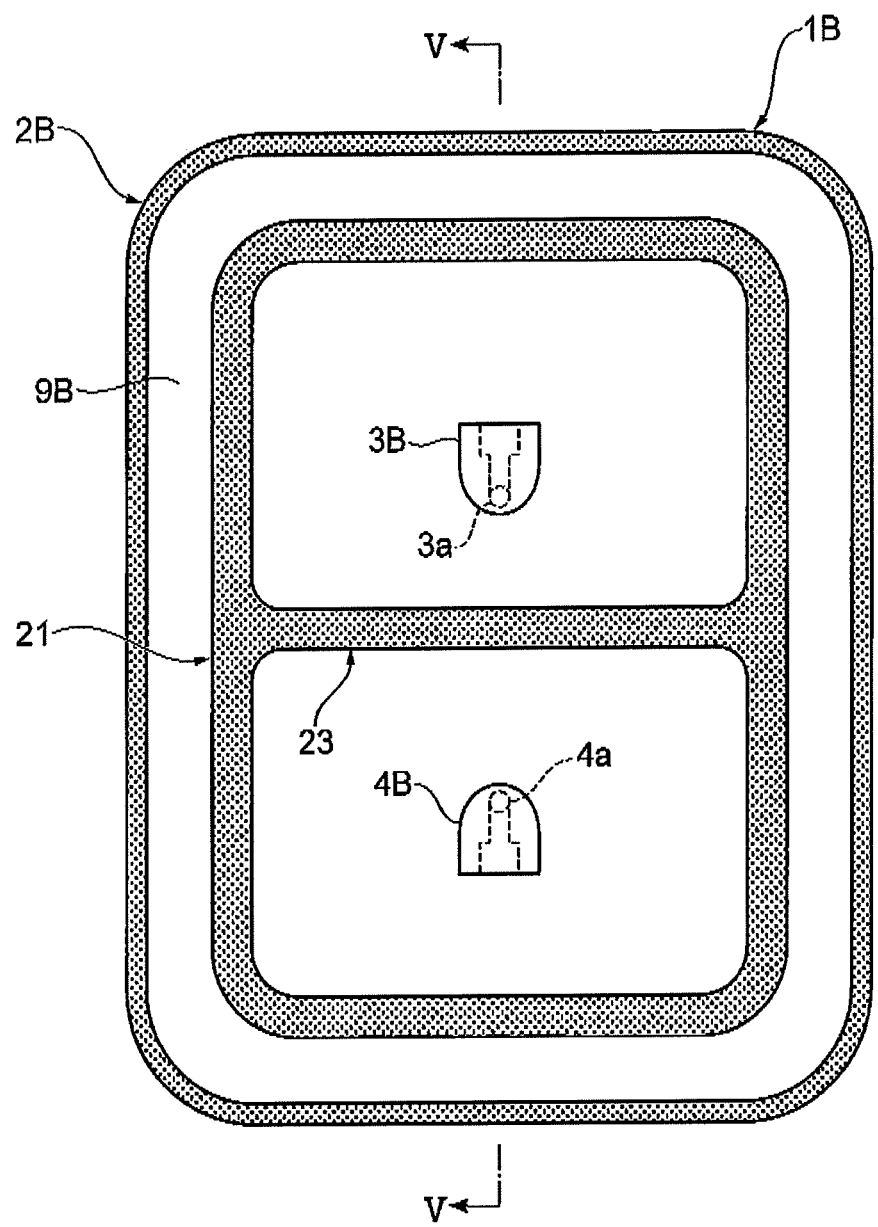
FIG. 4 is a plan view of a blood processing filter according to a second embodiment of the present invention.
Figure 5:
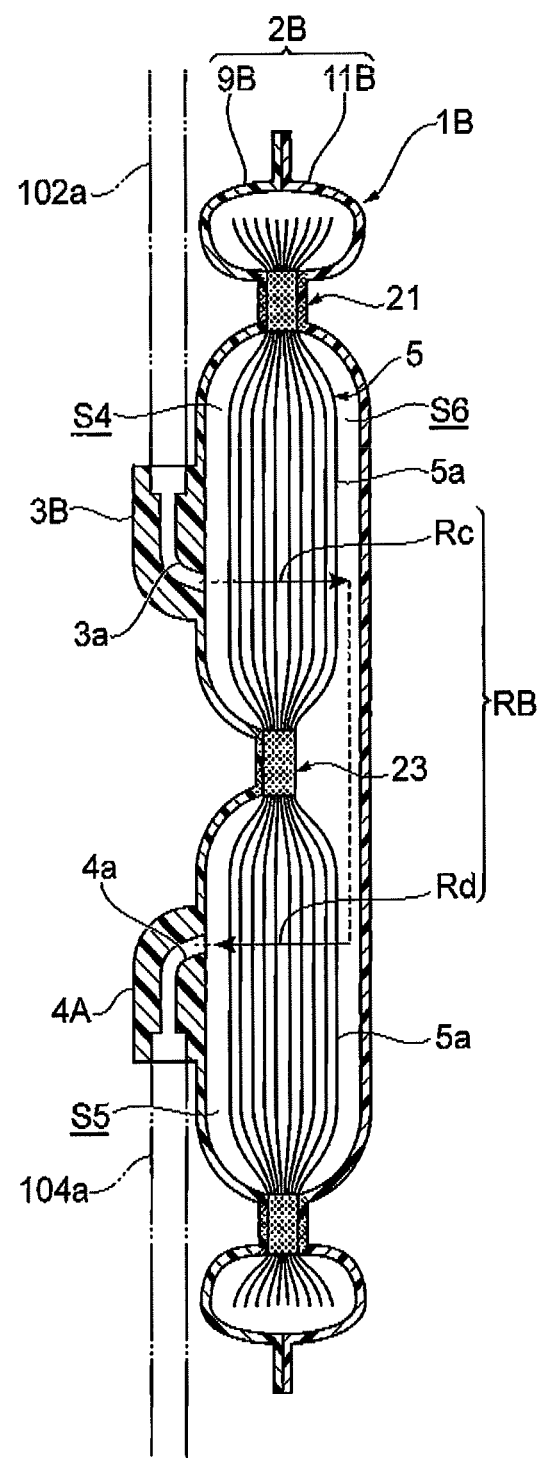
FIG. 5 is a cross-sectional view taken along a line V-V in FIG. 4.

Next, a blood processing filter according to a second embodiment of the present invention is described with reference to FIG. 4 and FIG. 5. FIG. 4 is a plan view of the blood processing filter according to the second embodiment of the present invention. FIG. 5 is a cross-sectional view taken along a line V-V in FIG. 4. A blood processing filter 1B according to the second embodiment includes substantially the same elements and structures as the blood processing filter 1A according to the first embodiment. Hence, elements and structures that are the same as in the first embodiment are denoted by the same reference symbols and a detailed description thereof is omitted, and the following description centers on elements and structures that are different from those of the first embodiment.

The blood processing filter 1B includes a flexible container 2B having an inlet port 3B and an outlet port 4B for blood, and the sheet-like filter member 5 that is assembled in the flexible container 2B. The flexible container 2B includes a first container forming part 9B that has a rectangular sheet shape, and a second container forming part 11B that has a rectangular sheet shape. The first container forming part 9B and the second container forming part 11B overlap in a manner that sandwiches the rectangular-shaped filter member 5 therebetween, and the peripheries of the first container forming part 9B and the second container forming part 11B closely contact each other and are sealed in a band shape.

The blood processing filter 1B also includes a seal part 21 and a partition part 23 that seal the flexible container 2B and the filter member 5 and divide the interior of the flexible container 2B into a plurality of internal spaces S4, S5, and S6 that include an inlet space S4 and an outlet space S5. The inlet space S4 is an internal space that communicates with the inlet flow channel 3a of the inlet port 3B. The outlet space S5 is an internal space that communicates with the outlet flow channel 4a of the outlet port 4B. The inlet space S4 and the outlet space S85 are formed on a side (one side) that faces the first container forming part 9B of the filter member 5. An intermediate space S6 that is a third internal space is formed on a side (other side) that faces the second container forming part 11B of the filter member 5.

The first container forming part 9B and the second container forming part 11B are sealed in a band shape along the periphery of the filter member 5 in a state in which the filter member 5 is clamped therebetween. A bonded area that is sealed in a rectangular ring shape along the periphery of the filter member 5 is the seal part 21.

Further, the first container forming part 9B and the filter member 5 are sealed in a band shape so as to divide the effective filtration portion 5a that is formed by the seal part 21 into two areas. A bonded area that is sealed so as to partition the effective filtration portion 5a is the partition part 23.

The seal part 21 and the partition part 23 according to the present embodiment cooperate with each area of the effective filtration portion 5a of the filter member 5 to form two internal spaces S4 and S5 on one side of the filter member 5, and to form an internal space S6 on the other side of the filter member 5 so that the number of internal spaces on the other side is one less than the number of internal spaces on the one side. Specifically, the inlet space S4 and the outlet space S5 are formed between the filter member 5 and the first container forming part 9B, and the intermediate space S6 is formed between the second container forming part 11B and the filter member 5. The intermediate space S6 is not partitioned by the partition part 23, and is provided so as to be capable of communicating with both of the inlet space S4 and the outlet space S5 through the filter member 5.

The surface area of the filter member 5 that is exposed inside the inlet space S4 is greater than the surface area of a region that communicates with the outlet space S5 within the surface area of the filter member 5 that is exposed inside the intermediate space S6.

The seal part 21 and the partition part 23 form, as a blood channel RB, a channel that passes through each of the internal spaces S4, S5, and S6, and also passes multiple times through the filter member 5. For example, as the blood channel RB, the seal part 21 and the partition part 23 form an outward channel Rc that passes through the filter member 5 from the inlet space S4 towards the intermediate space S6, and a return channel Rd that passes through the filter member 5 from the intermediate space S6 towards the outlet space S5. As a result, the blood channel RB passes through the internal spaces S4 and S5 formed on one side of the filter member 5 and the internal space S6 formed on the other side of the filter member 5 in alternating manner.

The flexible container 2B of the blood processing filter 1B that is described above can be formed by substantially the same materials as the flexible container 2A of the blood processing filter 1A according to the first embodiment. The blood processing filter 1B can also be applied to the blood processing system 100 in place of the blood processing filter 1A.

In the blood processing filter 1B, as the blood channel RB from the inlet flow channel 3a to the outlet flow channel 4a, a channel is formed that, while passing through the plurality of internal spaces S4, S5, and S6, also passes multiple times through the filter member 5. According to the blood processing filter 1B, even though the filter member 5 is thin, since blood passes through the filter member 5 multiple times, it can be expected that the capacity to remove leukocytes and the like will be equal to a case in which the filter member 5 is thick. That is, an effect that is equal to a case in which a thick filter member is used can be obtained by dividing the effective filtration portion 5a of the filter member 5, and this effect is advantageous in reducing the material required as the filter member 5. Furthermore, the capacity to remove leukocytes and the like can be maintained even though less material is used.

Further, from the viewpoint of assembling the blood processing filter 1B, even though the thin filter member 5 is used, an effect is obtained that is equal to an effect in the case of a form in which a small, thick filter member is used that is difficult to assemble. Accordingly, a welding workload when sealing the filter member 5 also decreases, and thus the blood processing filter 1B according to the present embodiment is also advantageous from the viewpoint of the assembly workload. Hence, advantages can be obtained in terms of ease of assembly and ease of sealing.

Figure 6:
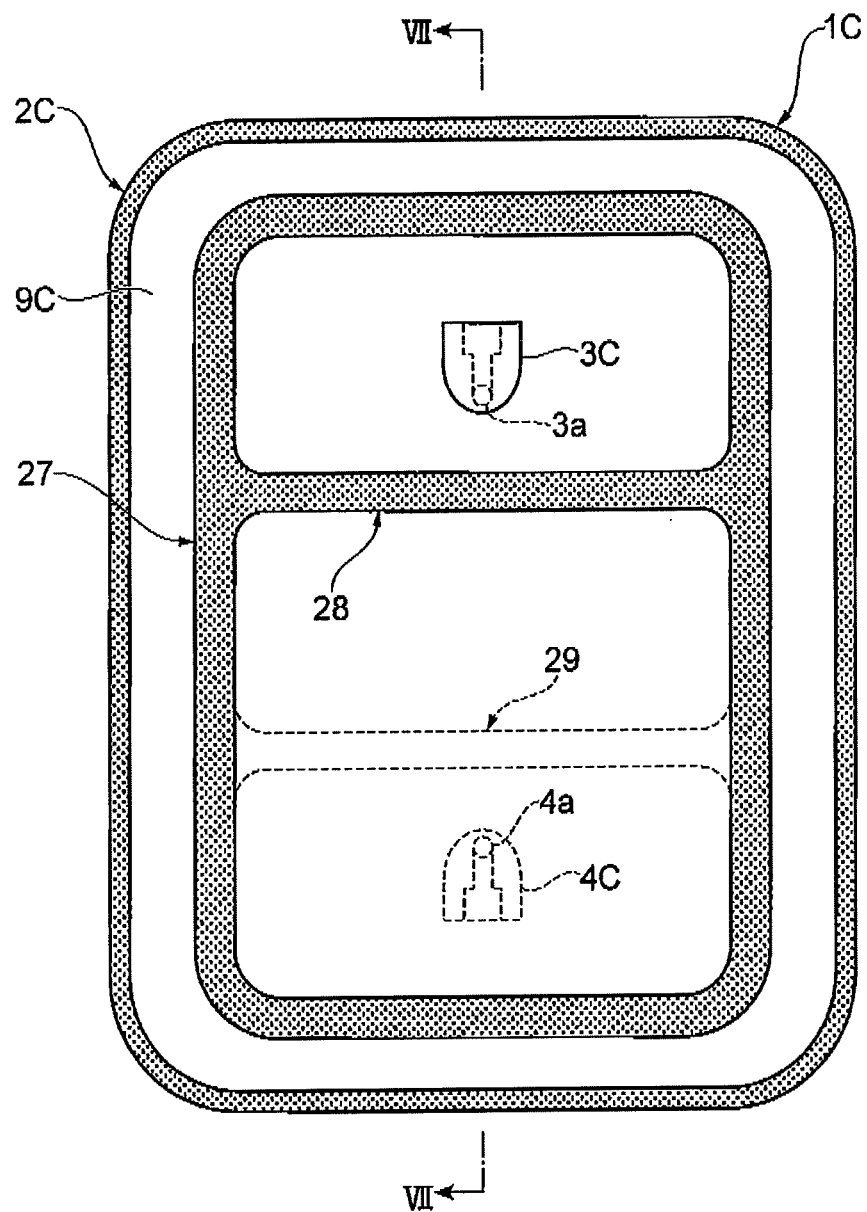
FIG. 6 is a plan view of a blood processing filter according to a third embodiment of the present invention.
Figure 7:
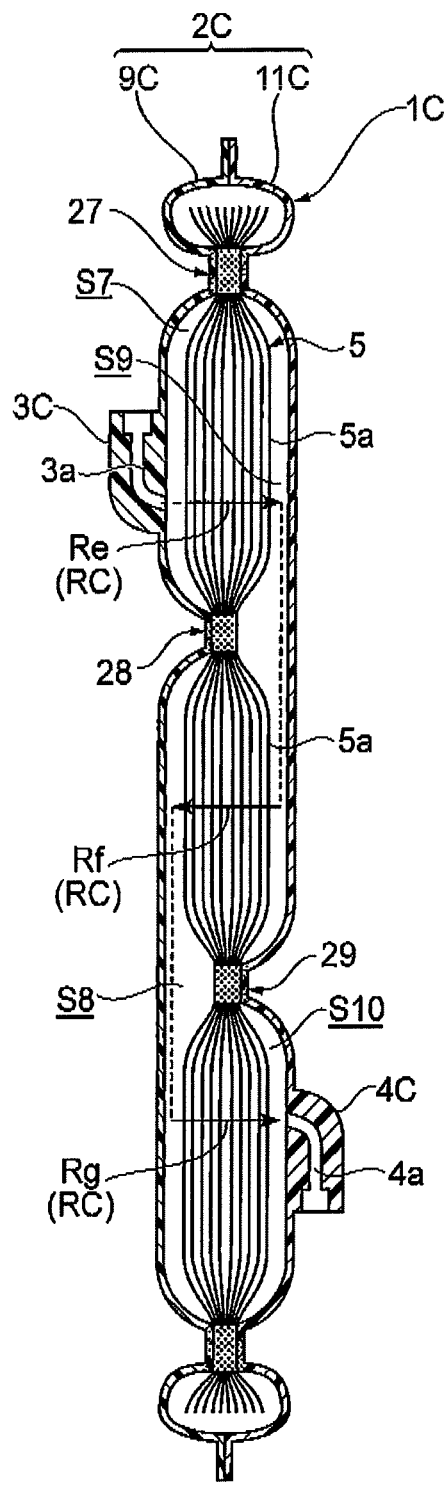
FIG. 7 is a cross-sectional view taken along a line VII-VII in FIG. 6.

Next, a blood processing filter according to a third embodiment of the present invention is described with reference to FIG. 6 and FIG. 7. FIG. 6 is a plan view of the blood processing filter according to the third embodiment of the present invention. FIG. 7 is a cross-sectional view taken along a line VII-VII in FIG. 6. A blood processing filter 1C according to the third embodiment includes substantially the same elements and structures as the blood processing filter 1A according to the first embodiment and the blood processing filter 1B according to the second embodiment. Hence, elements and structures that are the same as in the first or second embodiment are denoted by the same reference symbols and a detailed description thereof is omitted, and the following description centers on elements and structures that are different from the foregoing embodiments.

The blood processing filter 1C includes a flexible container 2C having an inlet port 3C and an outlet port 4C for blood, and the sheet-like filter member 5 that is assembled in the flexible container 2C. The flexible container 2C includes a first container forming part 9C that has a rectangular sheet shape, and a second container forming part 11C that has a rectangular sheet shape. The first container forming part 9C and the second container forming part 11C overlap in a manner that sandwiches the rectangular-shaped filter member 5 therebetween, and the peripheries of the first container forming part 9C and the second container forming part 11C closely contact each other and are sealed in a band shape. Note that, according to the present embodiment, the outlet port 4C is provided in the second container forming part 11C and not the first container forming part 9C.

The blood processing filter 1C also includes a seal part 27, a partition part 28, and a partition part 29 that seal the flexible container 2C and the filter member 5 and divide the interior of the flexible container 2C into a plurality of internal spaces S7, S8, 89 and S10 that include an inlet space S7 and an outlet space S10. The inlet space S7 is an internal space that communicates with the inlet flow channel 3a of the inlet port 3C. The outlet space S10 is an internal space that communicates with the outlet flow channel 4a of the outlet port 4C. The inlet space S7 and the internal space S8 are formed on a side (one side) that faces the first container forming part 9C of the filter member 5. The internal space S9 and the outlet space S10 are formed on a side (other side) that faces the second container forming part 11C of the filter member 5.

The first container forming part 9C and the second container forming part 11C are sealed in a band shape along a periphery of the filter member 5 in a state in which the filter member 5 is clamped therebetween. A bonded area that is sealed in a ring shape along the periphery of the filter member 5 is the seal part 27.

The first container forming part 9C and the filter member 5 are sealed in a band shape so as to partition an upper region of the effective filtration portion 5a that is surrounded by the seal part 27. A bonded area in which the first container forming part 9C and the filter member 5 are sealed so as to partition the upper region of the effective filtration portion 5a is the partition part 28.

Further, the filter member 5 and the second container forming part 11C are sealed in a band shape so as to partition a lower region of the effective filtration portion 5a that is surrounded by the seal part 27. A bonded area in which the filter member 5 and the second container forming part 11C are sealed so as to partition the lower region of the effective filtration portion 5a is the partition part 29.

The seal part 27 and the partition part 28 according to the present embodiment cooperate with each area of the effective filtration portion 5a of the filter member 5 to form two internal spaces S7 and S8 on one side of the filter member 5. Further, on the other side of the filter member 5, the seal part 27 and the partition part 29 form internal spaces S9 and S10, and thus the same number of internal spaces is formed on the other side as on the one side. Specifically, the inlet space S7 and an intermediate space S8 are formed between the filter member 5 and the first container forming part 9C, and an intermediate space S9 and the outlet space S10 are formed between the second container forming part 11C and the filter member 5. The intermediate space S9 is formed so as to straddle the partition part 28, and is provided so as to be capable of communicating with the inlet space S7 and the intermediate space S8 through the filter member 5. The intermediate space S8 is formed so as to straddle the partition part 29, and is provided so as to be capable of communicating with the intermediate space S9 and the outlet space S10 through the filter member 5.

The seal part 27, the partition part 28, and the partition part 29 form, as a blood channel RC, a channel that passes through each of the internal spaces S7, S8, S9, and S10, and also passes multiple times through the filter member 5. For example, in the case of the present embodiment, as the blood channel RC, the partition part 30 forms a first outward channel Re that passes through the filter member 5 from the inlet space S7 towards the intermediate space S9, a return channel Rf that passes through the filter member 5 from the intermediate space S9 towards the intermediate space S8, and a second outward channel Rg that passes through the filter member 5 from the intermediate space S8 towards the outlet space S10. As a result, the blood channel RC passes through the internal spaces S7 and S8 formed on one side of the filter member 5 and the internal spaces 59 and 510 formed on the other side of the filter member 5 in an alternating manner.

The flexible container 2C of the blood processing filter 1C that is described above can be formed by substantially the same materials as the flexible container 2A of the blood processing filter 1A according to the first embodiment. The blood processing filter 1C can also be applied to the blood processing system 100 in place of the blood processing filter 1A.

In the blood processing filter 1C, as the blood channel RC from the inlet flow channel 3a to the outlet flow channel 4a, a channel is formed that, while passing through the plurality of internal spaces S7, S8, S9 and S10, also passes multiple times through the filter member 5. According to the blood processing filter 1C, even though the filter member 5 is thin, since blood passes through the filter member 5 multiple times, it can be expected that the capacity to remove leukocytes and the like will be equal to a case in which the filter member 5 is thick. That is, an effect that is equal to a case in which a thick filter member is used can be obtained by dividing the effective filtration portion 5a of the filter member 5, and this effect is advantageous in reducing the material required as the filter member 5. Furthermore, the capacity to remove leukocytes and the like can be maintained even though less material is used.

Further, from the viewpoint of assembling the blood processing filter 1C, even though the thin filter member 5 is used, an effect is obtained that is equal to an effect obtained when adopting a form in which a small, thick filter member is used that is difficult to assemble. Accordingly, a welding workload when sealing the filter member 5 also decreases, and thus the blood processing filter 1C according to the present embodiment is also advantageous from the viewpoint of the assembly workload. Hence, advantages can be obtained in terms of ease of assembly and ease of sealing.

Figure 8:
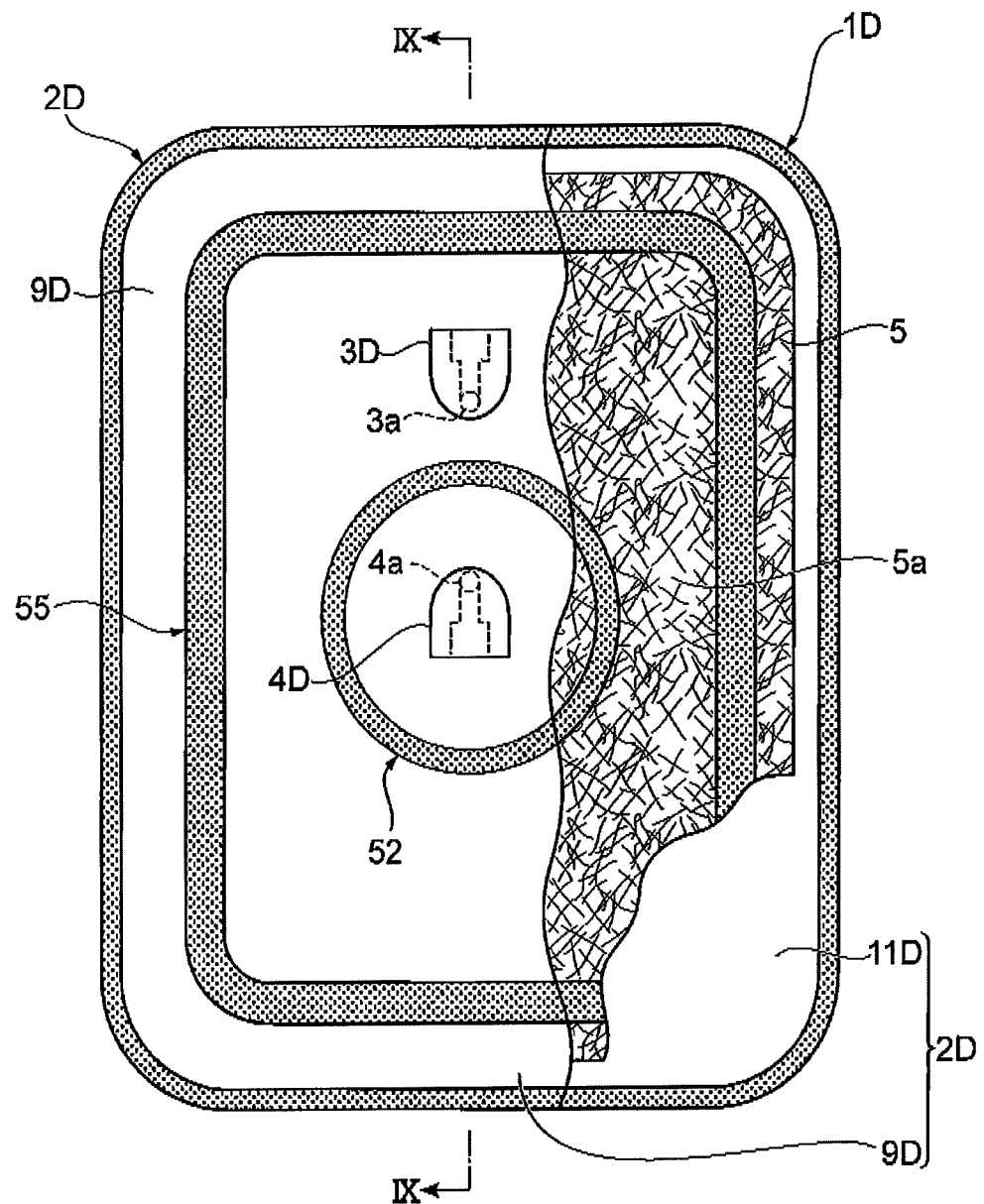
FIG. 8 is a plan view that illustrates one portion of a blood processing filter according to a fourth embodiment of the present invention, that is shown in a cut-away manner.
Figure 9:
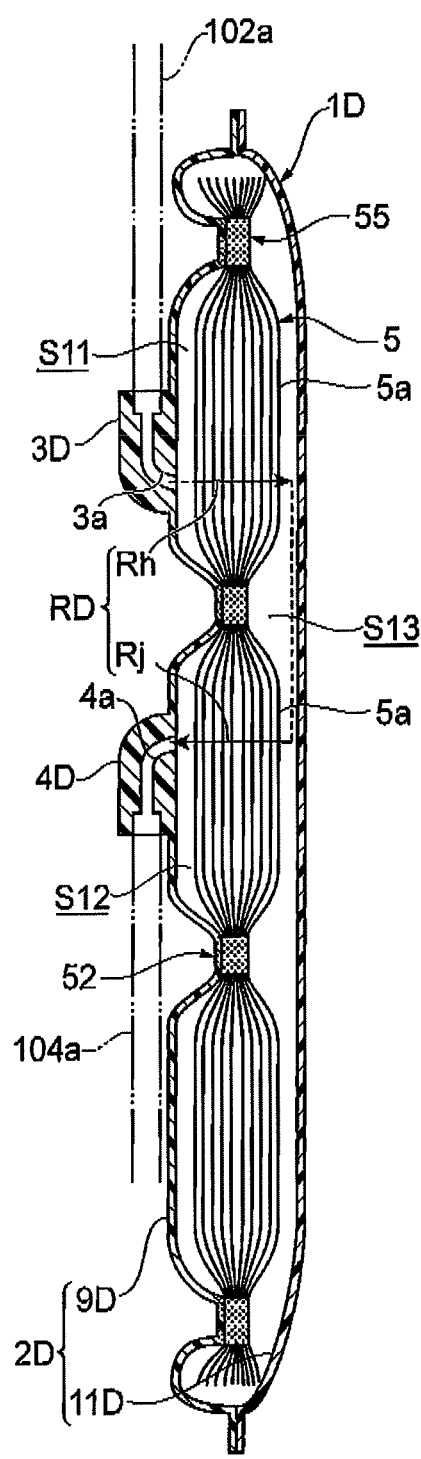
FIG. 9 is a cross-sectional view taken along a line IX-IX in FIG. 8.

Next, a blood processing filter according to a fourth embodiment of the present invention is described with reference to FIG. 8 and FIG. 9. FIG. 8 is a plan view of the blood processing filter according to the fourth embodiment of the present invention. FIG. 9 is a cross-sectional view taken along a line IX-IX in FIG. 8. A blood processing filter 1D according to the fourth embodiment includes substantially the same elements and structures as the blood processing filter 1A according to the first embodiment. Hence, elements and structures that are the same as in the first embodiment are denoted by the same reference symbols and a detailed description thereof is omitted, and the following description centers on elements and structures that are different from the first embodiment.

The blood processing filter 1D includes a flexible container 2D having an inlet port 3D and an outlet port 4D for blood, and the sheet-like filter member 5 that is assembled in the flexible container 2D. The flexible container 2D includes a first container forming part 9D that has a rectangular sheet shape, and a second container forming part 11D that has a rectangular sheet shape. The peripheries of the first container forming part 9D and the second container forming part 11D closely contact each other and are sealed in a band shape.

The blood processing filter 1D also includes a seal part 55 and a partition part 52 that seal the flexible container 2D and the filter member 5 and divide the interior of the flexible container 2D into a plurality of internal spaces S11, S12, and S13 that include an inlet space S11 and an outlet space S12. The inlet space S11 is an internal space that communicates with the inlet flow channel 3a of the inlet port 3D. The outlet space S12 is an internal space that communicates with the outlet flow channel 4a of the outlet port 4D. The inlet space S11 and the outlet space S12 are formed on a side (one side) that faces the first container forming part 9D of the filter member 5. The intermediate space S13 that is a third internal space is formed on a side (other side) that faces the second container forming part 11D of the filter member 5.

The first container forming part 9D and the filter member 5 are sealed in a band shape along a periphery of the filter member 5. A bonded area that is sealed in a rectangular ring shape along the periphery of the filter member 5 is the seal part 55. The effective filtration portion 5a of the filter member 5 is formed by the seal part 55.

The first container forming part 9D and the filter member 5 are sealed in a circular ring shape and in a band shape on an inner side that is surrounded by the seal part 55. A bonded area that is sealed in a ring shape on the inner side of the seal part 55 is the partition part 52.

The seal part 55 and the partition part 52 according to the present embodiment cooperate with each area of the effective filtration portion 5a of the filter member 5 to form two internal spaces S11 and S12 on one side of the filter member 5, and to form an internal space S13 on the other side of the filter member 5 so that the number of internal spaces on the other side is one less than the number of internal spaces on the one side. Specifically, the inlet space S11 and the outlet space S12 are formed between the filter member 5 and the first container forming part 9D, and the intermediate space S13 is formed between the filter member 5 and the second container forming part 11D. The intermediate space S13 is not partitioned by the partition part 52, and is provided so as to be capable of communicating with both of the inlet space S11 and the outlet space S12 through the filter member 5.

The surface area of the filter member 5 that is exposed inside the inlet space S11 is greater than the surface area of a region that communicates with the outlet space S12 within the surface area of the filter member 5 that is exposed inside the intermediate space S13.

In this connection, according to the present embodiment, the filter member 5 is not bonded to the second container forming part 11D, and rectangular ring-shaped recesses that correspond to the seal part 55 and the partition part 52 are formed on a side (other side) that faces the second container forming part 11D of the filter member 5. The recesses are formed as a result of the filter member 5 being compressed in a state in which the filter member 5 is in close contact with the first container forming part 9D, and being adhered in that state. Each recess is a valley part that is provided on the other side of the filter member 5.

The inlet port 3D and the outlet port 4D are sealed in the first container forming part 9D. The inlet flow channel 3a that serves as an inlet that communicates with inside of the flexible container 2D is formed in the inlet port 3D. The outlet flow channel 4a that serves as an outlet that communicates with inside of the flexible container 2D is formed in the outlet port 4D.

The seal part 55 and the partition part 52 form, as a blood channel RD, a channel that passes through each of the internal spaces S11, S12, and S13, and also passes multiple times through the filter member 5. For example, in the case of the present embodiment, as the blood channel RD, the partition part 52 forms an outward channel Rh that passes through the filter member 5 from the inlet space S11 towards the intermediate space S13, and a return channel Rj that passes through the filter member 5 from the intermediate space S13 towards the outlet space S12. As a result, the blood channel RD passes through the internal spaces S11 and S12 formed on one side of the filter member 5 and through the internal space S13 formed on the other side of the filter member 5 in an alternating manner.

Next, a method for manufacturing the blood processing filter 1D according to the present embodiment is described. According to this manufacturing method, for example, an installing step is performed in which the first container forming part 9D in which the inlet port 3D and the outlet port 4D have been sealed at predetermined positions and the filter member 5 are prepared, and the first container forming part 9D and the filter member 5 are arranged at predetermined positions.

After the installing step, a first sealing step is performed in which the partition part 52 is formed by sealing the first container forming part 9D and the filter member 5 in a band shape so as to surround the area in which the outlet port 4D is formed. Thereafter, a second sealing step is performed in which the rectangular ring-shaped seal part 55 is formed by sealing the first container forming part 9D and the filter member 5 so as to surround the partition part 52 along the periphery of the filter member 5.

Although formation of the partition part 52 in the first sealing step, more specifically, sealing of the first container forming part 9D and the filter member 5, can be performed utilizing high frequency welding, the present invention is not limited thereto, and various kinds of bonding techniques, such as ultrasonic welding or thermal welding, can be used. Likewise, although sealing to form the seal part 55 in the second sealing step can be performed utilizing high frequency welding, the present invention is not limited thereto, and various kinds of bonding techniques, such as ultrasonic welding or thermal welding, can be used. Note that the order of executing the first sealing step and the second sealing step may be reversed.

After the first sealing step and the second sealing step, a third sealing step is performed in which the first container forming part 9D and the second container forming part 11D are superimposed on each other so as to sandwich the filter member 5, and the peripheries of the first container forming part 9D and the second container forming part 11D are brought into close contact with each other and sealed in a band shape. Although sealing of the first container forming part 9D and the second container forming part 11D can be performed utilizing high frequency welding, the present invention is not limited thereto, and various kinds of bonding techniques, such as ultrasonic welding or thermal welding, can be used.

According to the above described manufacturing method, a form is described in which the inlet port 3D and the outlet port 4D are previously sealed to the flexible container 2D. However, sealing may be performed after forming the partition part 52 or the seal part 55, or may be performed during the process of forming the partition part 52 and the seal part 55. Further, a method of sealing the inlet port 3D and the outlet port 4D to the flexible container 2D is not limited to high frequency welding, and any kind of bonding technique, such as thermal welding, can be used. Similarly to the flexible container 2D, various known materials can be used as the material of the inlet port 3D and the outlet port 4D.

The flexible container 2D of the blood processing filter 1D that is described above can be formed by substantially the same materials as the flexible container 2A of the blood processing filter 1A according to the first embodiment. The blood processing filter 1D can also be applied to the blood processing system 100 in place of the blood processing filter 1A.

Next, the actions and effects of the blood processing filter 1D according to the present embodiment are described. In the blood processing filter 1D, as the blood channel RD from the inlet flow channel 3a to the outlet flow channel 4a, a channel is formed that, while passing through the plurality of internal spaces S11, S12, and S13, also passes multiple times through the filter member 5. According to the blood processing filter 1D, even though the filter member 5 is thin, since blood passes through the filter member 5 multiple times, it can be expected that the capacity to remove leukocytes and the like will be equal to a case in which the filter member 5 is thick. That is, an effect that is equal to a case when using a thick filter member can be obtained by dividing the effective filtration portion 5a of the filter member 5, and this effect is advantageous in reducing the material required as the filter member 5. Furthermore, the capacity to remove leukocytes and the like can be maintained even though less material is used.

Further, from the viewpoint of assembling the blood processing filter 1D, even though the thin filter member 5 is used, an effect is obtained that is equal to an effect obtained when adopting a form in which a small, thick filter member is used that is difficult to assemble. Accordingly, a welding workload when sealing the filter member 5 also decreases, and thus the blood processing filter 1D according to the present embodiment is also advantageous from the viewpoint of the assembly workload. Hence, advantages can be obtained in terms of ease of assembly and ease of sealing.

Further, according to the blood processing filter 1D, a first filtration (primary filtration) is performed when blood passes through the filter member 5 in the outward channel Rh of the blood channel RD, and a second filtration (secondary filtration) is performed when blood passes through the filter member 5 in the return channel Rj of the blood channel RD. During the primary filtration, removal of aggregates and the like is principally performed, and during the secondary filtration only blood from which aggregates and the like have been removed is filtered. In this case, in the primary filtration a certain filtration area is necessary because there is a loss due to entry of aggregates and the like. On the other hand, in the secondary filtration, since the blood that is filtered has undergone filtration once and contains no aggregates and has a reduced amount of leukocytes, a filtration area that is smaller than the filtration area on the primary filtration side is sufficient for the secondary filtration side. Furthermore, in the blood processing filter 1D, since an area ratio between the filtration area on the primary filtration side and the filtration area on the secondary filtration side can be made an arbitrary area ratio, the area ratio can be optimized with ease. That is, according to the blood processing filter 1D, not only can the number of sheets of nonwoven fabric and the like constituting the filter member 5 as well as the overall area thereof be optimized in accordance with the blood to be filtered, the usage conditions, and required performance, but it is also possible to arbitrarily optimize the area ratio between the filtration area on the primary filtration side and the filtration area on the secondary filtration side.

Further, in the blood processing filter 1D, since the intermediate space S13 exists between the outlet space S12 and the inlet space S11, when performing a filtration process, a negative pressure that arises in the outlet space S12 can be alleviated and uniform filtration can be performed.

In this connection, although according to the present embodiment a member is not adhered or the like on the one side or the other side of the filter member 5 in correspondence with the partition part 52 or the seal part 55, a configuration may also be adopted in which a frame sheet or the like for maintaining the strength of the partition part 52 or the seal part 55 is sealingly integrated with the filter member 5.

Further, a configuration may also be adopted in which a flow channel securing sheet in which a flow channel hole is formed is arranged so as to overlap with the effective filtration portion 5a on the other side of the filter member 5, and the flow channel securing sheet is, for example, sealingly integrated with the filter member 5 at the seal part 55. By providing the flow channel securing sheet, it is difficult for the filter member 5 and the second container forming part 11D to come into close contact with each other even if a gap arises between the filter member 5 and the second container forming part 11D in the intermediate space S13 and a negative pressure arises in the intermediate space S13 during a filtration process. Thus, performance of uniform filtration is facilitated. In this connection, a similar flow channel securing sheet can also be arranged in the outlet space S12. In such case, close contact between the filter member 5 and the first container forming part 9D is prevented and performance of uniform filtration is facilitated.

What is claimed is:

1. A blood processing filter comprising:
a flexible container having an inlet and an outlet for blood, a sheet-like filter member that is assembled in the flexible container, a seal part that seals the flexible container and the filter member to form an effective filtration portion of the filter member, a partition part that seals the flexible container and the filter member to partition the effective filtration portion into a plurality of areas;
wherein the sheet-like filter member has a continuous peripheral edge, the seal part is formed so as to be continuous, and the seal part and the partition part cooperate with the filter member to divide inside of the flexible container into three or more internal spaces including an inlet space that communicates with the inlet and an outlet space that communicates with the outlet, and the seal part and the partition part cooperating with the filter member to provide a blood channel defined by a channel that passes through each of the three or more internal spaces and passes multiple times through the filter member, and,
in a plan view of the flexible container, the partition part is formed continuously and surrounds the outlet of the flexible container.

2. The blood processing filter according to claim 1, wherein:
the flexible container comprises a first container forming part and a second container forming part that overlaps with the first container forming part in a manner that sandwiches the filter member therebetween, the second container forming part being sealed to the first container forming part; and
the seal part and the partition part form a plurality of the internal spaces on one side of the filter member and form at least one of the plurality of the internal spaces on an other side of the filter member, and the channel that defines the blood channel passes through the plurality of internal spaces formed on the one side of the filter member and through the at least one of the plurality of internal spaces formed on the other side of the filter member in an alternating manner.

3. The blood processing filter according to claim 2, wherein the seal part and the partition part form the plurality of the internal spaces including the inlet space and the outlet space on the one side of the filter member and, on the other side of the filter member, form the internal spaces in a number that is one less than a number of the internal spaces on the one side of the filter member.

4. The blood processing filter according to claim 2, wherein the seal part and the partition part form the plurality of the internal spaces including the inlet space on the one side of the filter member and, on the other side of the filter member, form the internal spaces in a number that is identical to a number of the internal spaces on the one side of the filter member that include the outlet space.

5. The blood processing filter according to claim 2, wherein the seal part and the partition part form the inlet space and the outlet space on the one side of the filter member and, on the other side of the filter member, form an intermediate space configured to communicate with both of the inlet space and the outlet space through the filter member, and that channel that defines the blood channel passes through the inlet space, the intermediate space, and the outlet space.

6. The blood processing filter according to claim 5, wherein a surface area of the filter member that is exposed in the inlet space is greater than a surface area of a region that communicates with the outlet space within a surface area of the filter member that is exposed inside the intermediate space.

7. The blood processing filter according to claim 1, wherein, in a plan view of the flexible container, the continuous seal part surrounds the inlet and the outlet of the flexible container.

8. The blood processing filter according to claim 1, wherein, in a plan view of the flexible container, the inlet and the outlet of the flexible container are positioned within the continuous peripheral edge of the sheet-like filter member.

9. The blood processing filter according to claim 1, wherein the sheet-like filter member is defined by a single member extending continuously between outer peripheral edges of the flexible container.

* * * * *